(12) United States Patent
Gregg et al.

(10) Patent No.: US 11,826,251 B2
(45) Date of Patent: Nov. 28, 2023

(54) CARDIAC VALVE DELIVERY DEVICES AND SYSTEMS

(71) Applicant: Cephea Valve Technologies, Inc., Santa Clara, CA (US)

(72) Inventors: Peter Gregg, Santa Cruz, CA (US); Evelyn N. Haynes, Soquel, CA (US); Dan Wallace, Santa Cruz, CA (US); Aaron Grogan, Scotts Valley, CA (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 565 days.

(21) Appl. No.: 16/962,932

(22) PCT Filed: Jan. 18, 2019

(86) PCT No.: PCT/US2019/014349
§ 371 (c)(1),
(2) Date: Jul. 17, 2020

(87) PCT Pub. No.: WO2019/147504
PCT Pub. Date: Aug. 1, 2019

(65) Prior Publication Data
US 2020/0345493 A1 Nov. 5, 2020

Related U.S. Application Data

(60) Provisional application No. 62/621,692, filed on Jan. 25, 2018.

(51) Int. Cl.
*A61F 2/24* (2006.01)
*A61F 2/95* (2013.01)
(Continued)

(52) U.S. Cl.
CPC .......... *A61F 2/2436* (2013.01); *A61F 2/9517* (2020.05); *A61F 2002/9505* (2013.01);
(Continued)

(58) Field of Classification Search
CPC .... A61F 2/2436; A61F 2/2439; A61F 2/9517; A61F 2/962; A61F 2/966;
(Continued)

(56) References Cited

U.S. PATENT DOCUMENTS 5,201,757 A * 4/1993 Heyn ........................ A61F 2/97
606/198
8,518,098 B2 * 8/2013 Roeder ..................... A61F 2/97
606/108

(Continued)

FOREIGN PATENT DOCUMENTS

WO 201618352 A1 2/2016
WO 2016168609 A1 10/2016
(Continued)

OTHER PUBLICATIONS

Extended European Search Report for EP Appln. No. 19743415.2 dated Nov. 3, 2021 (pp. 1-7).
(Continued)

*Primary Examiner* — Diane D Yabut
(74) *Attorney, Agent, or Firm* — SLEMAN & LUND LLP

(57) ABSTRACT

A prosthetic valve delivery device includes a handle and a delivery catheter. The delivery catheter includes a central elongate member extending from the handle and a proximal sheath configured to slide over and relative to the central elongate member. The proximal sheath is connected to a hollow helical strand, and the hollow helical strand is configured to rotate to retract the proximal sheath and expose at least a portion of the prosthetic valve.

25 Claims, 17 Drawing Sheets

(51) Int. Cl.
*A61M 25/00* (2006.01)
*A61M 25/01* (2006.01)

(52) U.S. Cl.
CPC . *A61F 2220/0041* (2013.01); *A61F 2230/005* (2013.01); *A61F 2230/0091* (2013.01); *A61F 2250/0065* (2013.01); *A61M 25/0054* (2013.01); *A61M 25/0147* (2013.01)

(58) Field of Classification Search
CPC ...... A61F 2002/9505; A61F 2220/0041; A61F 2230/005; A61F 2230/0091; A61F 2250/0065; A61M 25/0147; A61M 25/0054
See application file for complete search history.

(56) References Cited

U.S. PATENT DOCUMENTS

| | | | |
|---|---|---|---|
| 8,870,948 B1 | 10/2014 | Erzberger et al. | |
| 2006/0286145 A1* | 12/2006 | Horan | A61F 2/95 424/426 |
| 2011/0307049 A1* | 12/2011 | Kao | A61F 2/966 623/1.11 |
| 2012/0150289 A1 | 6/2012 | Forster et al. | |
| 2013/0103130 A1* | 4/2013 | Lubinski | A61F 2/966 623/1.11 |
| 2013/0158655 A1 | 6/2013 | Sutton et al. | |
| 2014/0067050 A1 | 3/2014 | Costello et al. | |
| 2014/0214154 A1 | 7/2014 | Nguyen et al. | |
| 2014/0343670 A1* | 11/2014 | Bakis | A61F 2/2436 623/2.11 |
| 2015/0142100 A1* | 5/2015 | Morriss | A61F 2/246 623/2.4 |
| 2016/0158000 A1 | 6/2016 | Granada et al. | |
| 2018/0028305 A1* | 2/2018 | von Oepen | A61F 2/2436 |
| 2018/0126119 A1* | 5/2018 | McNiven | A61M 25/0136 |
| 2018/0126124 A1* | 5/2018 | Winston | A61M 25/0052 |

FOREIGN PATENT DOCUMENTS

| | | | |
|---|---|---|---|
| WO | 2016183523 A1 | 11/2016 | |
| WO | 2018094069 A1 | 5/2018 | |

OTHER PUBLICATIONS

International Search Report and Written Opinion for PCT Application PCT/US2019/014349 dated Apr. 12, 2019.

* cited by examiner

CARDIAC VALVE DELIVERY DEVICES AND SYSTEMS

CROSS REFERENCE TO RELATED APPLICATIONS

This application is a national phase entry under 35 U.S.C. § 371 of International Application No. PCT/US2019/147504, filed on Jan. 18, 2019, which claims priority to U.S. Provisional Patent Application No. 62/621,692, filed Jan. 25, 2018, entitled "TRANS SEPTAL CARDIAC VALVE DELIVERY DEVICES AND SYSTEMS," the disclosures of which are hereby incorporated by reference herein.

This application may also be related to International Patent Application No. PCT/US2016/032546, filed May 13, 2016 and titled "CARDIAC VALVE DELIVERY DEVICES AND SYSTEMS" and to International Patent Application No. PCT/US2017/62045, filed Nov. 16, 2017, the entireties of which are incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present invention relates generally to the treatment of cardiac valve disorders, such as mitral valve replacement, using minimally invasive techniques. In particular, this application is directed towards devices for delivering and placing replacement mitral valves.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Prosthetic valve replacement procedures can be difficult, and various factors are generally taken into account when placing the valve. First, the prosthetic valve should be placed at the same or very nearly the same angle as the native valve. A valve that is off axis could cause turbulent blood flow and/or potential para-valvular leaks. Second, the prosthetic valve should ideally have concentricity. This means that the valve is placed in the same center as the native valve. An off center deployment or valve placement could affect the mechanism of neighboring valves or the heart's conductive system. Finally, the prosthetic valve should be at the proper depth within the patient's heart with respect to the location of the native valve, as otherwise, the prosthetic valve may interfere with the conductive nature of the heart as well.

A safe and efficient delivery system and method for replacement of a cardiac valve that addresses some or all of these concerns is described herein.

SUMMARY OF THE DISCLOSURE

In general, in one embodiment, a prosthetic valve delivery device includes a handle and a delivery catheter. The delivery catheter includes a central elongate member extending from the handle and a proximal sheath configured to slide over and relative to the central elongate member. The proximal sheath is connected to a hollow helical strand, and the hollow helical strand is configured to rotate to retract the proximal sheath and expose at least a portion of the prosthetic valve.

This and other embodiments can include one or more of the following features. The delivery device can further include a valve retainer at a distal end of the central elongate member. The valve retainer can be a florette. The proximal sheath can be connected to the hollow helical strand with a nut. The handle can include a control configured to retract the proximal sheath. The delivery system can further include a distal sheath. The distal sheath can be configured to move distally to expose at least a portion of the prosthetic valve. The distal sheath can be connected to a compression coil. The compression coil can be configured to be pushed distally to move the distal sheath distally. The handle can include a control configured to move the distal sheath. The distal sheath can have a nosecone at a distal end thereof. The delivery system can further include a steering catheter configured to be positioned radially over the delivery catheter. The steering catheter can include a steerable distal end. The steerable distal end can include a plurality of articulating segments. The delivery system can further include a plurality of pullwires. Each pullwire can be connected to a different articulating segment to control articulation of the distal end. The handle can further include a control configured to steer the steerable distal end. The delivery system can further include an introducer configured to be positioned radially over the steering catheter. The introducer can further include a bent or bendable distal section. The introducer can be configured to be axially and rotationally movable relative to the steering catheter. The delivery system can further include a sealing valve between the steering catheter and the introducer. The handle can include three portions including a delivery catheter portion, a steering catheter portion, and an introducer portion. The delivery catheter portion and the steering catheter portion can be connected together with a telescoping tube such that the delivery catheter portion is axially movable relative to the steering catheter portion. The steering catheter portion and the introducer portion can be connected together with a telescoping tube such that the introducer portion is axially and rotationally movable relative to the steering catheter portion.

In general, in one embodiment, a prosthetic valve delivery device includes a handle, a delivery catheter, and a steering catheter configured to be positioned radially over the delivery catheter. The steering catheter includes a steerable distal end. The delivery catheter includes a central elongate member extending from the handle and a sheath configured to slide over and relative to the central elongate member.

This and other embodiments can include one or more of the following features. The delivery device can further include a valve retainer at a distal end of the central elongate member. The valve retainer can be a florette. The sheath can be a proximal sheath. The proximal sheath can be configured to retract proximally to expose at least a portion of the prosthetic valve. The proximal sheath can be connected to a hollow helical strand. The hollow helical strand can be configured to rotate to retract the proximal sheath. The proximal sheath can be connected to the hollow helical strand with a nut. The handle can include a control configured to retract the proximal sheath. The delivery system can further include a distal sheath. The distal sheath can be configured to move distally to expose at least a portion of the prosthetic valve. The distal sheath can be connected to a compression coil. The compression coil can be configured to be pushed distally to move the distal sheath distally. The handle can include a control configured to move the distal sheath. The distal sheath can have a nosecone at a distal end thereof. The steerable distal end can include a plurality of articulating segments. The delivery system can further include a plurality of pullwires. Each pullwire can be connected to a different articulating segment to control articulation of the distal end. The handle can further include a control configured to steer the steerable distal end. The delivery system can further include an introducer configured to be positioned radially over the steering catheter. The introducer can include a bent or bendable distal section. The introducer can be configured to be axially and rotationally movable relative to the steering catheter. The delivery system can further include a sealing valve between the steering catheter and the introducer. The handle can include three portions comprising a delivery catheter portion, a steering catheter portion, and an introducer portion. The delivery catheter portion and the steering catheter portion can be connected together with a telescoping tube such that the delivery catheter portion is axially movable relative to the steering catheter portion. The steering catheter portion and the introducer portion can be connected together with a telescoping tube such that the introducer portion is axially and rotationally movable relative to the steering catheter portion.

In general, in one embodiment, a method of delivering a prosthetic mitral valve includes using any of the delivery devices described herein to transseptally deliver a prosthetic mitral valve.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

The delivery devices described herein can be used to deliver and deploy a wide variety of replacement heart valves, such as prosthetic valves adapted to be minimally invasively delivered. Exemplary prosthetic valves that can be delivered and deployed with the delivery devices described herein include the expandable prosthetic valves described in U.S. application Ser. No. 14/677,320, filed Apr. 2, 2015, in U.S. Pat. No. 8,870,948, and in International Patent Application filed May 13, 2016, titled "REPLACEMENT MITRAL VALVES," and in U.S. patent application Ser. No. 14/677,320, filed Apr. 2, 2015, titled "REPLACEMENT CARDIAC VALVES AND METHODS OF USE AND MANUFACTURE," all of which are incorporated by reference herein. For example, the delivery devices herein can be configured to deliver and deploy a replacement heart valve, such as a mitral valve, that includes distal and proximal anchors.

Replacement heart valves can be collapsed into a delivery configuration so they can fit within the delivery devices described herein. The replacement heart valves can be delivered to the treatment site within the delivery devices and then deployed. The delivery devices can be configured such that the distal and proximal anchors can be sequentially deployed as desired from a collapsed configuration to an expanded configuration. If necessary, the replacement valves can be repositioned, re-sheathed (partially or completely) if necessary, and then re-deployed using the same delivery device.

The delivery devices described herein can be used to deliver the mitral valve prosthesis through the transseptal route, i.e., through the venous system and into the left atrium via a transseptal puncture. During the transseptal delivery, the distal-most anchor can be delivered to the ventricle while the proximal-most anchor can be delivered to the atrium.

In some embodiments, delivery devices such as those described herein designed for use in the transseptal route can have a long elongate body that is more flexible and has a smaller diameter than the elongate bodies of delivery devices used for the transatrial route.

Figure 1:
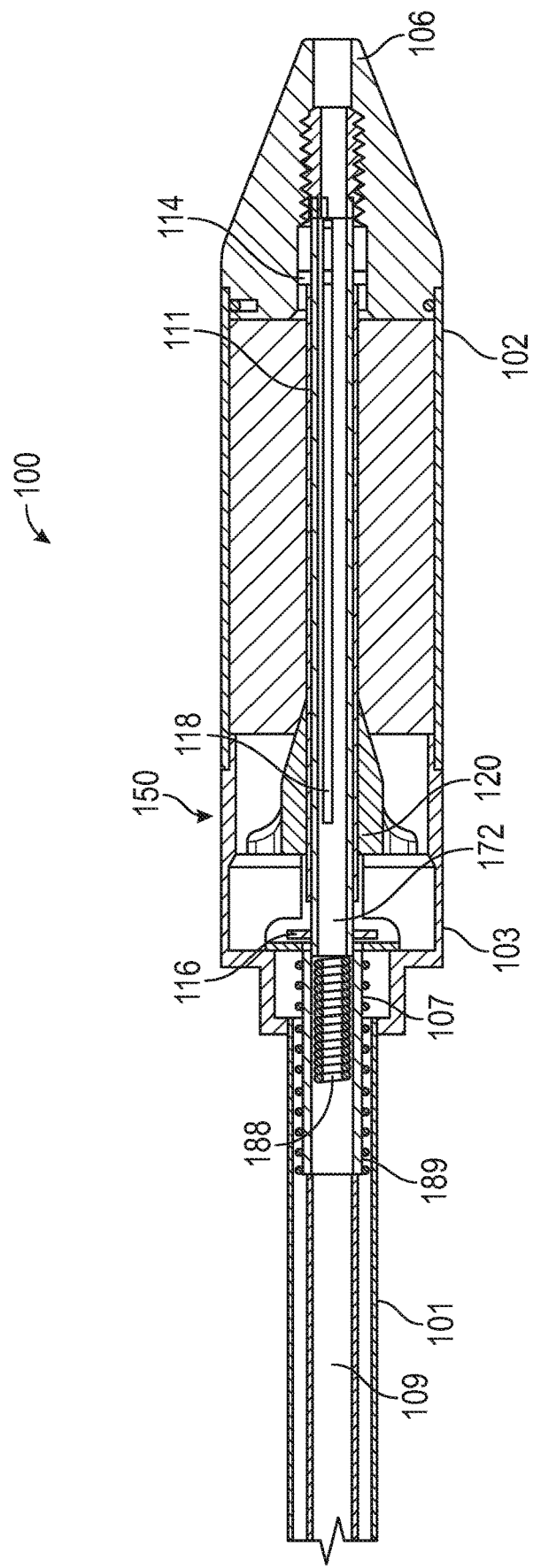
FIG. 1 shows the distal portion of an exemplary transseptal delivery catheter.

The distal portion of an exemplary transseptal delivery catheter 100 is shown in FIG. 1. The catheter 100 can include a distal control assembly 150 attached to a hollow helical strand 189 with a nut 107. A compression coil 188 can extend within the hollow helical strand 189. The distal control assembly 150 can include a split sheath including a distal sheath 102 and a proximal sheath 103. The distal sheath 102 can be connected to a tapered nosecone 106 while the proximal sheath 103 can be connected to the nut 107, which has threads that are compatible with the strands of the hollow helical strand 189. In some embodiments, the distal nosecone 106 can be configured to screw on and off to provide options for valve loading. An inner hypotube 172 can extend within the compression coil 188 and/or the helical strand 189, ending at and attached to the nosecone 106. Further, a middle hypotube 111 can extend over the inner hypotube 172 and can end in a cap 114. A tether or valve retainer 120 configured as a florette can be attached to the middle hypotube 111. An outer hypotube 101 can extend over the compression coil 188 and hollow helical strand 189. The outer hypotube 101 can be laser cut and can be welded to the proximal sheath 103. Further, the outer hypotube 101 can be flexible so as to bend easily and/or conform to an outer steering catheter (as described further below).

The compression coil 188 can butt up against (and/or be welded to) the inner hyptotube 172 and can be used to push forward the nosecone 106 and distal sheath 102 to perform the first stage of valve deployment (e.g., ventricular anchor deployment). Further, a differentially spiral cut tube 109 can butt up against and be welded to the hollow helical strand 189. The spiral cut tube 109 can be more flexible where it travels through tighter curvature (e.g., towards the distal end of the catheter 100). Pushing and pulling the tube 109 at the proximal end of the assembly allows the user to insert and retract the distal control assembly 150 to adjust the depth of the prosthesis (e.g., to optimize deployment height of the prosthetic valve relative to the native annulus).

In use, the valve can be loaded into the delivery catheter 100 such that the distal anchor sits within the distal sheath 102 and the proximal anchor is positioned within the proximal sheath 103 and the loops of the proximal anchor extend around the raised portions of the florette 120. Once the delivery catheter 100 has been guided to the atrium and the prosthesis positioned relative to the native annulus, the distal sheath 102 can be pushed distally by pushing on the compression coil 188 to extend the inner hypotube 172. Pushing the distal sheath 102 distally can cause the distal anchor to be released in the ventricle. The middle hypotube 111 can shield the packed valve from the motion of the inner hypotube 172 when extending the distal sheath 102. Further, in some embodiments, a slit 118 in the inner hyptotube 172 can prevent over extension of the distal sheath 102 into the anatomy. Specifically, the proximal end of the slit 118 can hit the end cap 114 to prevent over extension of the distal sheath 102. The distance limit can ensure that there are always rigid, concentric bodies linking the two sheaths 102, 103, making re-assembly easier and avoiding excessive motion in the ventricle. Further, the cap 114 can interface with the slit 118 to lock the retainer 120 and distal sheath 102 rotationally, minimizing rotation against the loaded valve. The hypotube 172 can keep the distal sheath 102 rigidly aligned and concentric with the proximal sheath 103.

After the distal sheath 102 has been pushed distally, the proximal sheath 103 can be pulled proximally to release the proximal anchor in the atrium. The proximal sheath 103 can be pulled proximally, for example, by rotating the helical strand 189 such that the external threads interact with the nut 107 to cause the sheath 103 to retract. The outer hypotube 101 can be free to move axially during movement of the control assembly 150 (i.e., during axial movement of the hollow helical strand 189). However, the outer hypotube 101 can be keyed to prevent its own rotation and therefore prevent rotation of the proximal sheath 103. Further, a fitting lock 116 can be attached to the distal end of the hollow helical strand 189. The fitting lock 116 can translate push-pull of the hollow helical strand to insert/retract the control assembly 150 while allowing the retainer 120, middle hypotube 111, and distal sheath 102 to remain stationary rotationally and in the same axial position while the hollow helical strand 189 rotates to retract the proximal sheath 103. The hollow helical strand 189 can advantageously provide flexibility as the device 100 bends while providing fine control and mechanical advantage when loading the valve or deploying the proximal anchor.

Following deployment of the valve, the hollow helical strand 189 can be rotated in the opposite direction to move the proximal sheath 103 distally through the valve's leaflets. This can be supplemented by pushing the hollow helical strand 189 distally to move both sheaths 102, 103 distally. The distal sheath 102 can then be retracted by pulling on the compression coil 188. The control assembly 150 can then be retracted through the valve by pulling on the tube 109.

Figures 2A, 2B:
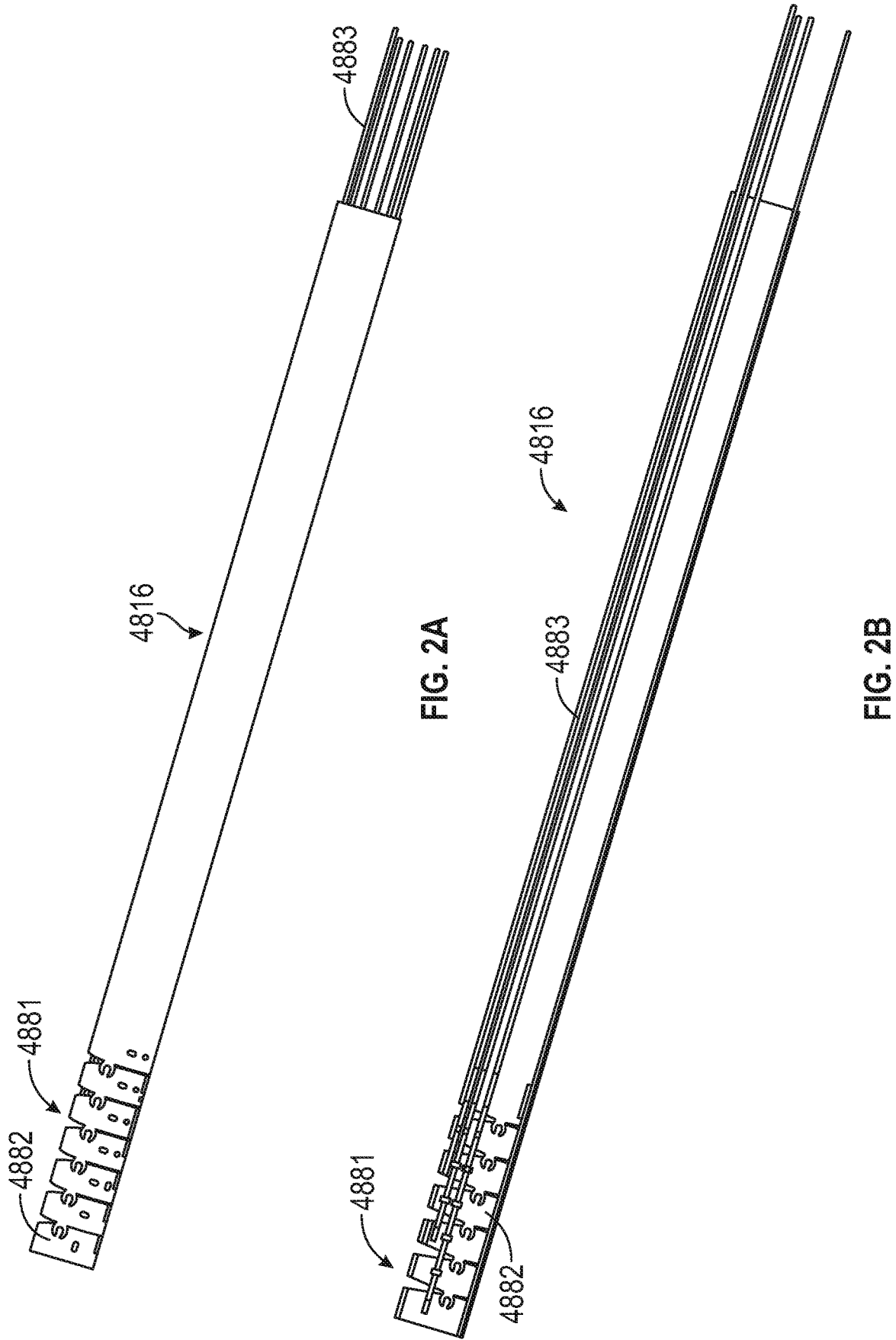
FIGS. 2A-2C show an exemplary steering catheter for use with a delivery catheter.
Figure 2C:
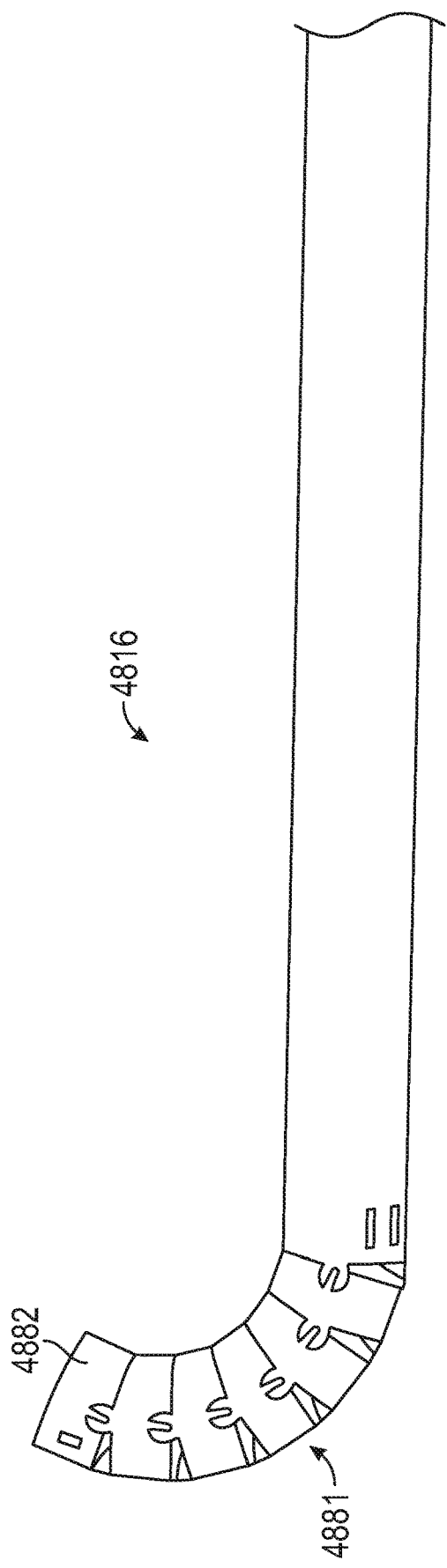
Figure 3B:
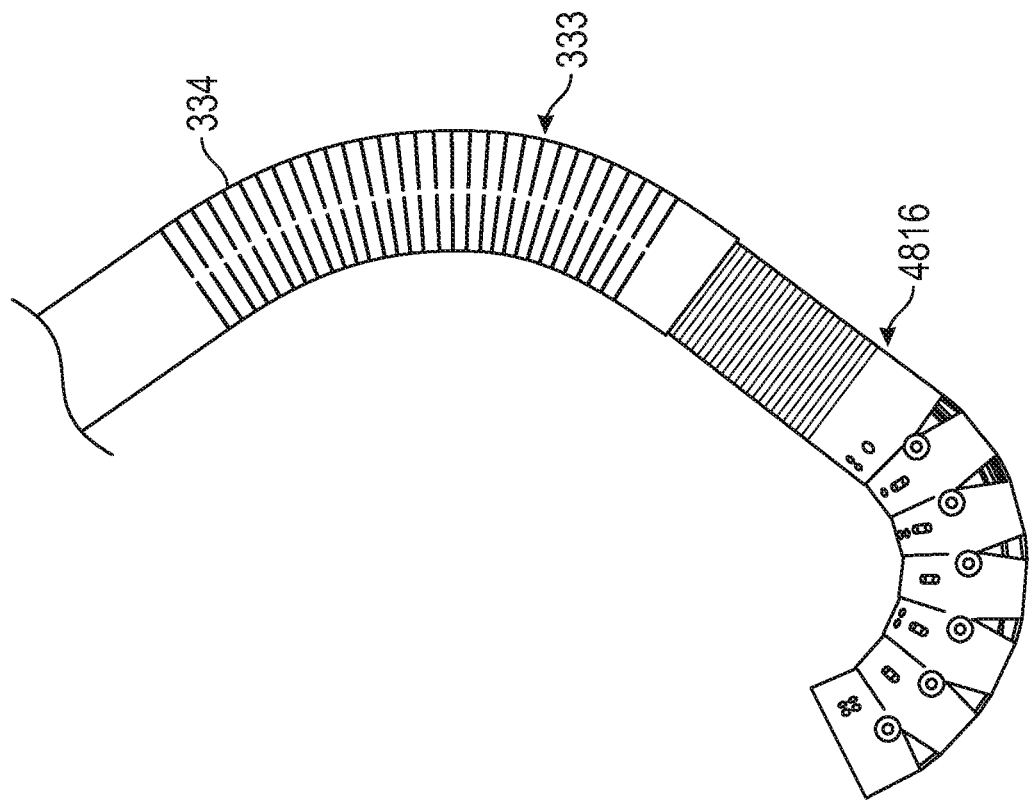
FIGS. 3A-3D show an introducer sheath over the steering catheter of FIGS. 2A-2C.
Figure 3A:
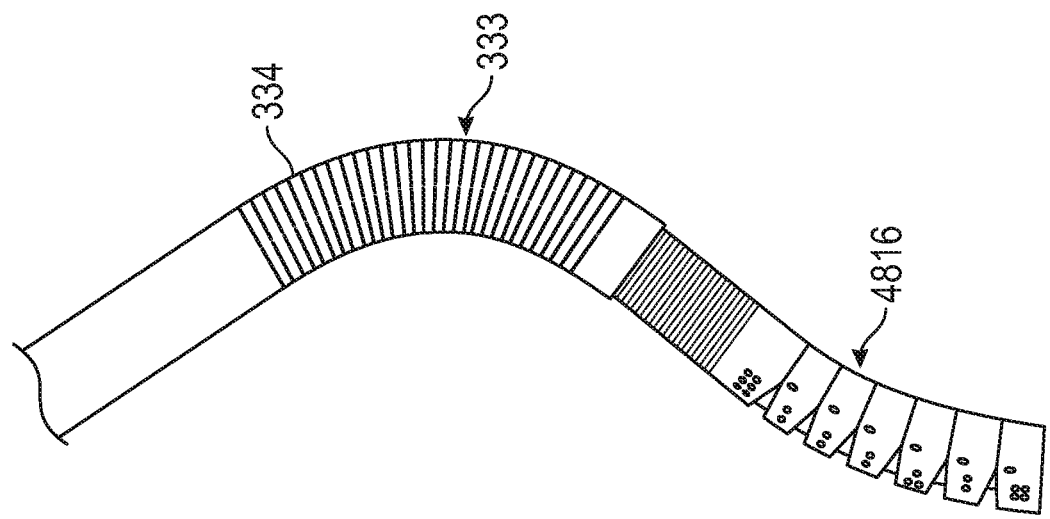
Figure 3D:
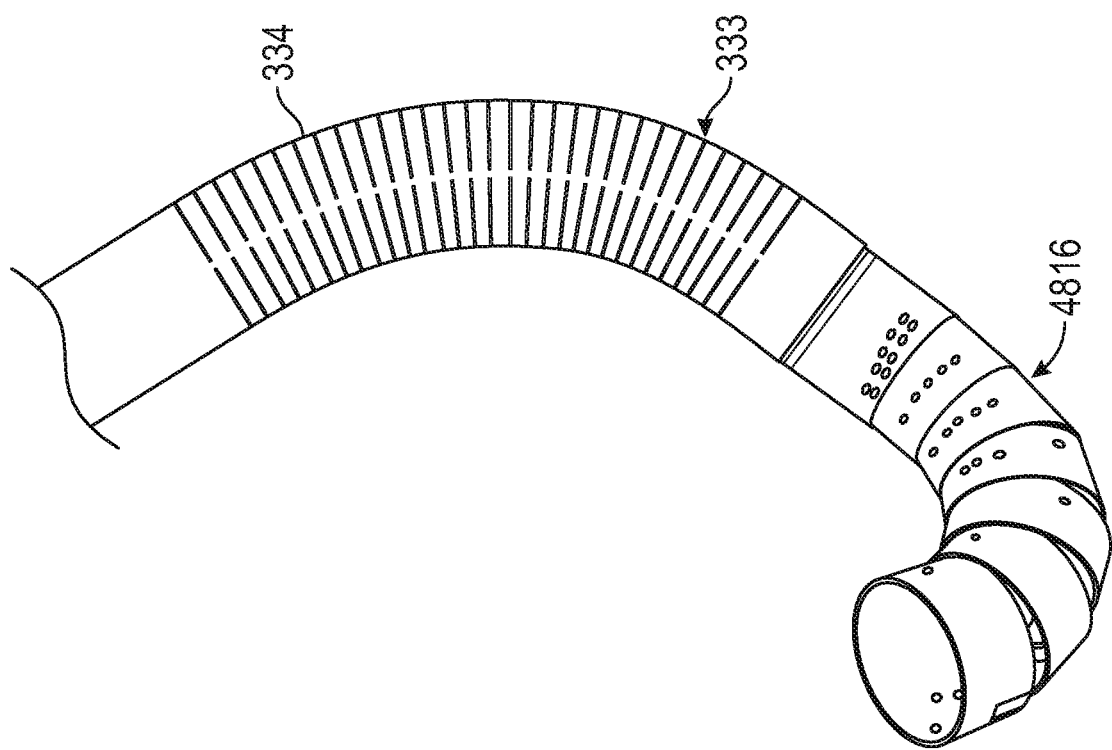
Figure 3C:
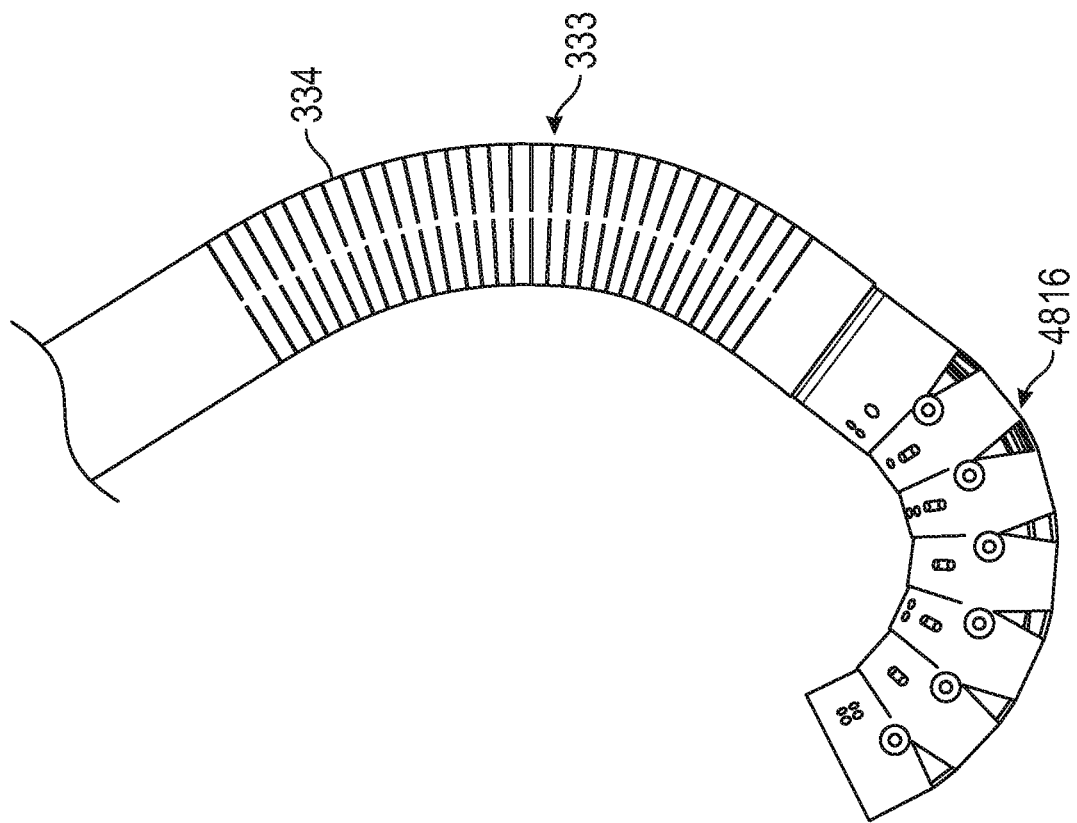

An exemplary steering catheter 4816 for use with a delivery catheter (such as catheter 100) is shown in FIGS. 2A-2C. The outer steering catheter 4816 includes a flexible distal end 4881. The flexible distal 4881 end includes a plurality of articulating segments 4882. A series of pullwires 4883 extend along the length of the steering catheter 4816 to the articulating segments 4882 for controlling the bending of each segment 4882, thereby providing for controllable maneuverability of the distal end 4881. In one embodiment (and as best shown in FIG. 2B), one pullwire 4883 terminates at every other segment 4882 such that three pullwires 4883 control the angles of six articulating segments 4882. Using multiple pullwires 4883 provides more determinate control of the articulation angles. Similarly, an embodiment with one pullwire terminating at each articulating segment could result in fully determinate articulation with each articulating segment pivoting to a determined angle under pullwire control. Other ratios of pullwires to segments are possible with a decrease in determinate articulating segment angle control as the ratio of pullwires to segments decreases. FIG. 2C shows the distal end 4881 in a bent configuration (i.e., activated by the pullwires 4883). In some embodiments, the articulating segments 4882 can be formed from a laser cut tube in a ball and socket formation. There can be pullwires 4883 attached on opposite sides of each segment 4882 to allow for controlling directionality with full determinacy. Further, the pullwires 4883 can be supported by compression coils such that the distal segments 4882 articulate without creating bending in the proximal length of the catheter 4816. Eyelets on an inner surface of the articulating segments 4882 can guide the pullwires 4883 to create a known path and help avoid interference with distal mechanisms running through the center of the delivery catheter. The flexible distal end 4881 can advantageously aid in advancing the steering catheter 4816 through the tortuous venous system.

Referring to FIGS. 3A-3D, in some embodiments, an introducer sheath 333 can be used over the steering catheter 4816. The introducer sheath 333 can be configured to move axially and rotationally relative to the steering catheter 4816 (e.g., the introducer sheath 333 can be held stationary relative to the patient while the steering catheter 4816 can move therein), making the system adaptable to a wide range of anatomy relative to fixed distances and relative angles between the two curves. The introducer sheath 333 can have a bent or bendable portion 334, which can also be controlled with one or more pullwires. The bent or bendable portion 334 can be configured to be positioned in the right atrium during delivery. The introducer sheath 333 and the steering catheter 4816 can include one or more valves, such as a duck valve or a hemo stasis valve, therebetween to ensure proper sealing. In some embodiments, both a duck valve and a dome seal can be used. Having a duck valve and dome seal together ensures sealing: (1) with just the introducer sheath 333 placed; (2) while inserting the delivery catheter through the introducer sheath 333; and (3) when the delivery catheter is in place and being inserted or rotated in the introducer sheath 333. Ensuring hemostasis during exchanges means more of the procedure (e.g., trans-septal puncture, wire placement, closure prep) can happen while the introducer 333 is in place.

Figure 4:
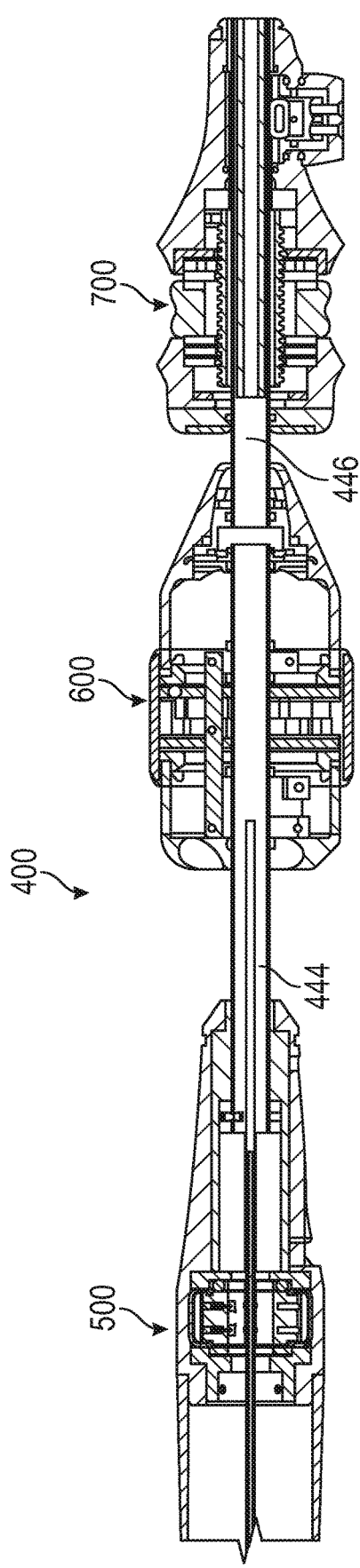
FIG. 4 shows a handle system for controlling a delivery catheter, a steering catheter, and an introducer.

An exemplary handle system 400 for a transseptal delivery system as described herein is shown in FIG. 4. The handle system 400 includes a delivery catheter handle 500, a steering catheter handle 600, and an introducer handle 700. A rigid telescoping tube 444 extends between the delivery catheter handle 500 and the steering catheter handle 600 to allow for axial movement of the delivery catheter handle 500 over the tube 444 and relative to the steering catheter handle 600, thereby providing for insertion of the distal control assembly (e.g., assembly 150 of catheter 100) and valve. A second rigid telescoping tube 446 can extend between the steering catheter handle 600 and the introducer handle 700 to allow the curves of the steering catheter (e.g., steering catheter 4816) and the introducer sheath (e.g., sheath 333) to be moved relative to one another to provide for compatibility with varying anatomies. The telescoping tube 446 can form the body of the steering catheter and can be designed so as to be progressively more flexible from the proximal end to the distal end until reaching the articulating segments. Additionally, the steering catheter handle 600 and introducer handle 700 can rotate relative to one another so as to change the direction of the curves of the steering catheter and introducer independently.

Figure 5A:
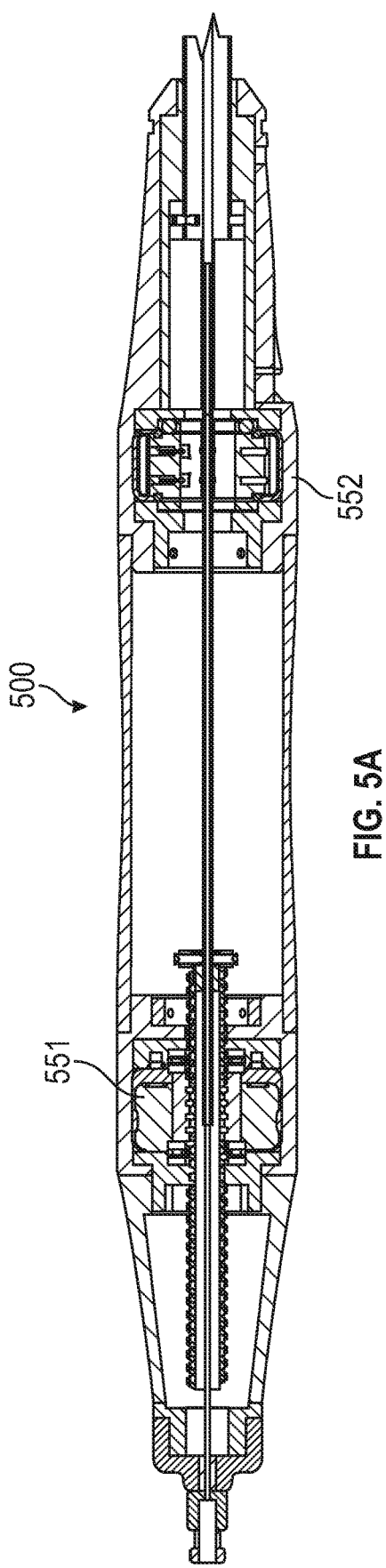
FIGS. 5A-5C shows the delivery catheter handle of the system of FIG. 4.
Figure 5B:
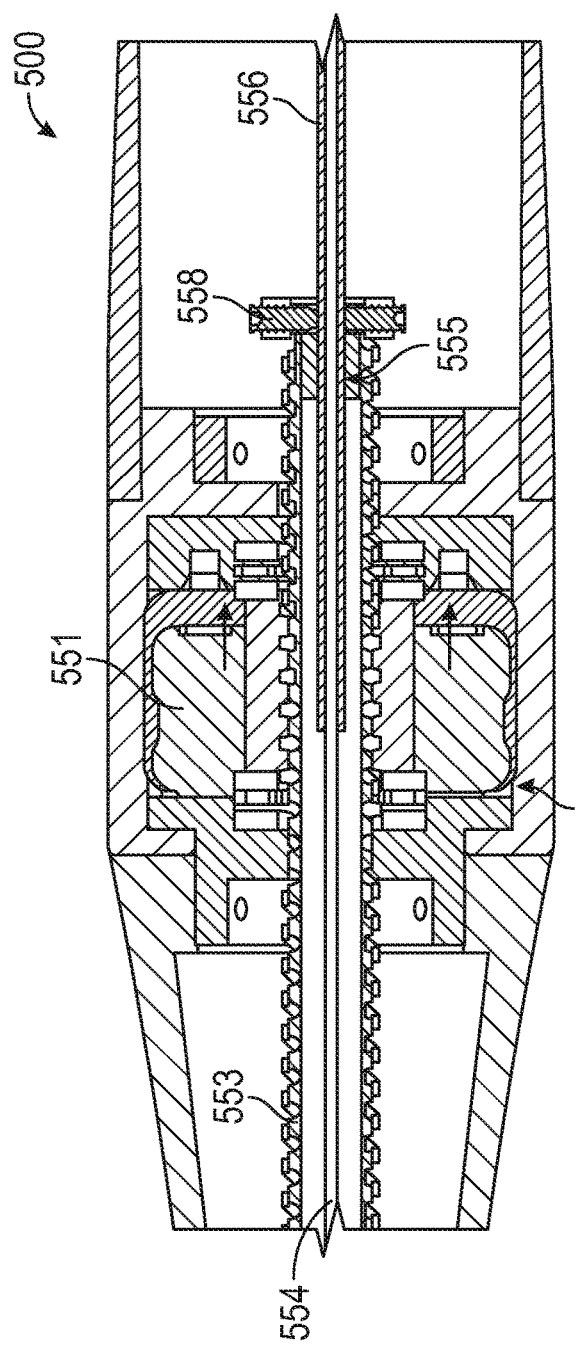
Figure 5C:
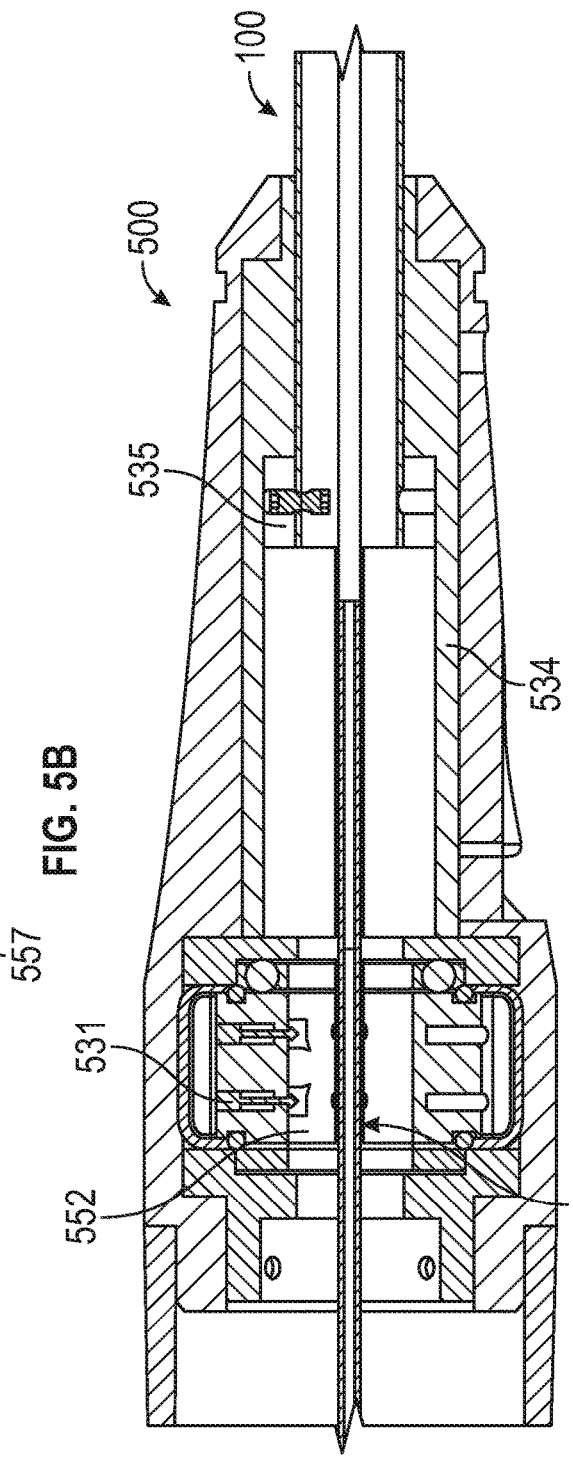

Referring to FIGS. 5A-5C, the delivery catheter handle 500 (of system 400) can be configured to attach to the delivery catheter 100. The handle 500 can include a first knob 551 that can rotate to extend or retract the compression coil 188 attached to the distal sheath 102 (e.g., for deploying the distal anchor of the valve). A second knob 552 can rotate to spin the hollow helical strand 189 to extend or retract the proximal sheath 103 (e.g., for deploying the proximal anchor). As shown best in FIG. 5B, the handle 500 can further include a lead screw 553 with a guidewire tube 554 telescoping therethrough (the tube 109 can connect to the lead screw 553). The knob 551 can include ratchet features 557 that lock forward/distal motion of the lead screw to apply constant pressure on the compression coil 188 while advancing the distal sheath 102. Further, the knob 551 can be configured to move distally to a free spinning configuration to pull the compression coil 188 and distal sheath 102 proximally. A compression coil hypotube 556 can be rigid in the handle 500 and be welded to the compression coil 188. Two set screws 558 on a threaded ring can pass through the lead screw 553 and press against or fit into machined features on the compression coil hypotube 556 to lock linear motion of the compression coil hypotube 556. As best shown in FIG. 5C, the handle 500 can further include a series of set screws 531 to lock rotation of the inner and outer portions of the second knob 552. A hypotube 533 in the handle 500 can be welded to the central portion of the knob 552 and can be attached to the hollow helical strand 189 (e.g., just before the distal bends in the steering catheter 4816 and the introducer sheath 333). A boss 535 can support and limit the telescoping of the rigid telescoping tube 444. The boss 535 can be keyed to prevent rotation between the steering catheter 4816 and the delivery catheter 100. An insert 534 in the handle 500 can be keyed to the boss 535 and can set a travel limit for the telescoping of the tube 444 that extends between the delivery catheter handle 500 and the steering catheter handle 600.

Figure 6A:
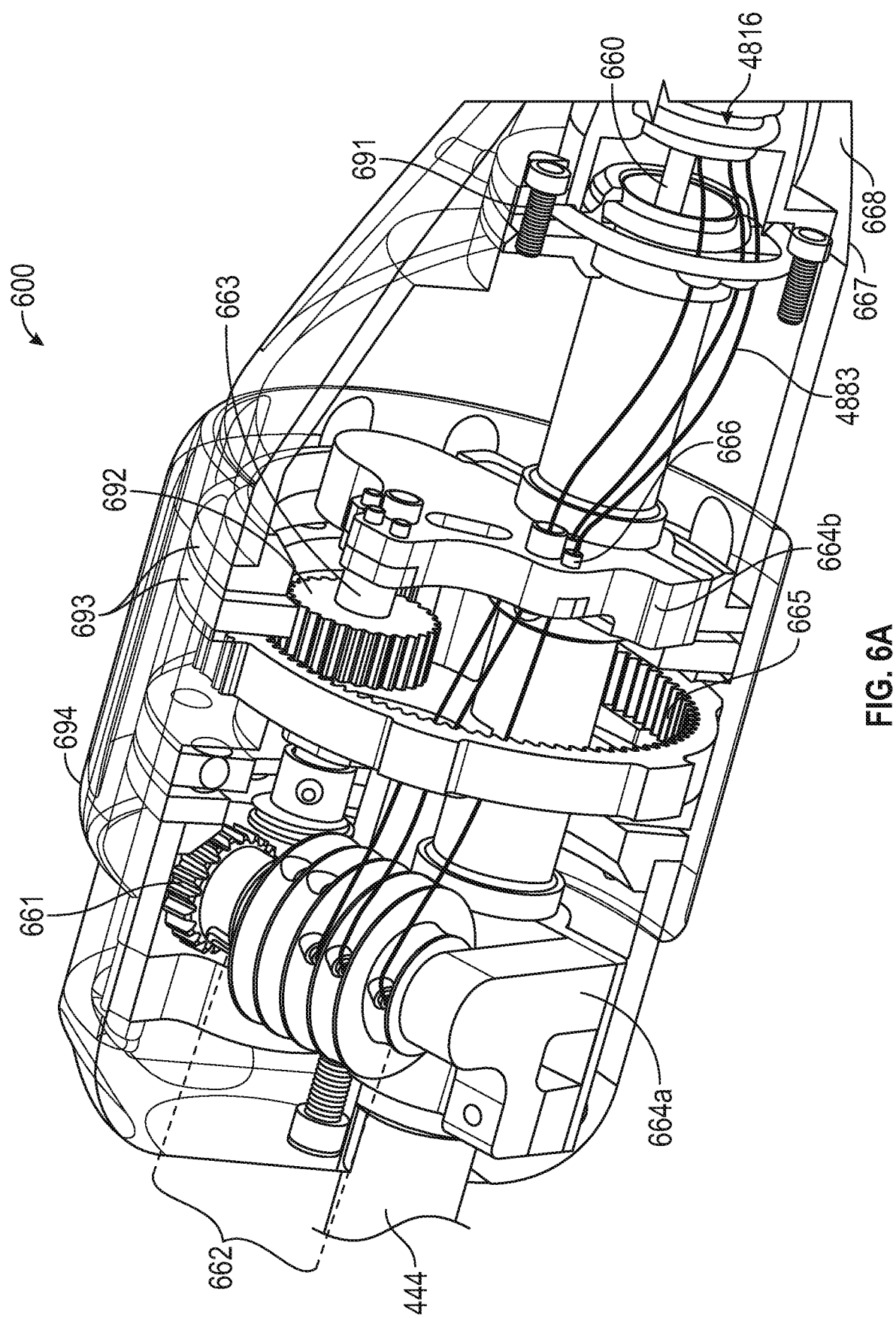
FIGS. 6A-6C show the steering catheter handle of the system of FIG. 4.

Referring to FIG. 6A, the steering catheter handle 600 (of system 400) can be configured to attach to the steering catheter 4816. The steering catheter handle 600 can include a knob 694 that can activate articulation of the distal curve/bend of the steering catheter 4816. The knob 694 can wrap 360° around the handle 600 so that rotating the handle 600 itself doesn't block movement of the knob 694. In some embodiments, the knob 694 can be rotated slightly over 360° to get full articulation. The knob 694 can be configured to turn an internal gear 665 having internal teeth therein. Keyed features can lock rotation of the knob 694 and the internal gear 665. A spur gear 692 can mate with the internal gear 665 and can rotate therewith. The spur gear 692, in turn, can turn the shaft 663, which can turn a worm gear 661. The worm gear 661 can rotate to rotate the spool stack 662 around which the pullwires 4883 are wound. This, in turn, can cause retraction/extension of the pullwires 4883 of the steering catheter 4816 to cause flexion of the steering catheter 4816. In some embodiments, the gear system of the handle 600 can create a 15:1 gear ratio, which can help prevent slip and provide mechanical advantage when activating the pullwires 4883. The telescoping tube 444 can extend through the handle 600. Two supports 664a,b can extend on either side of the internal gear 665 and can clamp onto the telescoping tube 444. The first support 664a can hold the spool stack 662 while the second support 664b can have holes therein to allow for passage of the pullwires 4483 therethrough without tangling. Ball bearings and a race plate 693 can be used to reduce friction as the gear system is activated. Angled set screws 691 can secure the hemostasis junction assembly in place on the handle assembly 600. O-rings in the assembly can further maintain hemostasis by blocking leak paths around the ends of the tubes 446 and 444 and around the pullwires 4883. Further, all of the distal tip assembly controls can run through the tube 444 without being impacted by the mechanics of the steering handle 600.

Figure 6B:
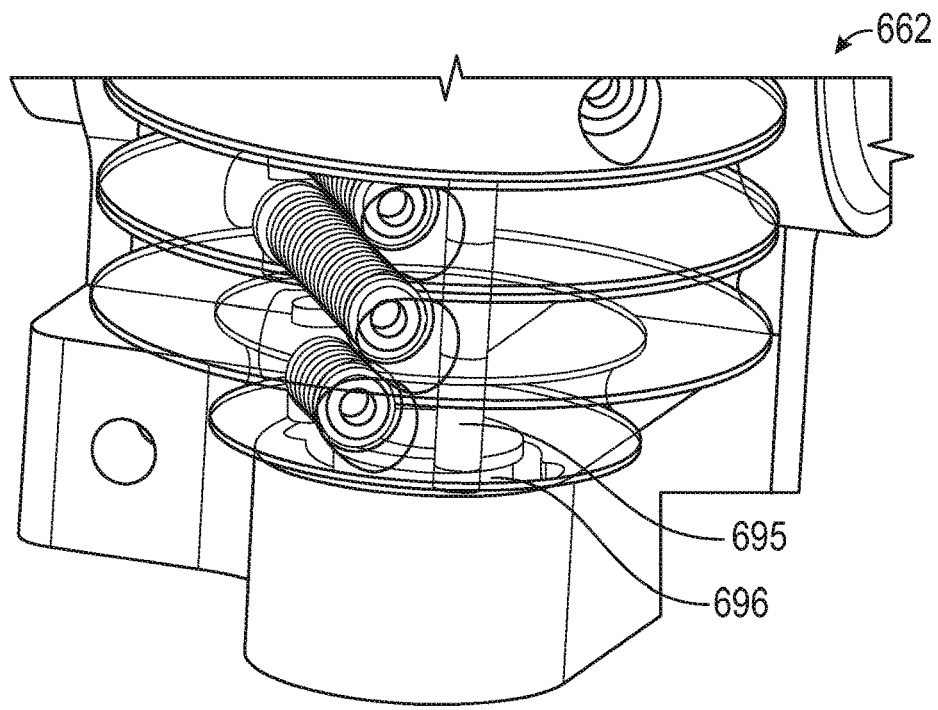
Figure 6C:
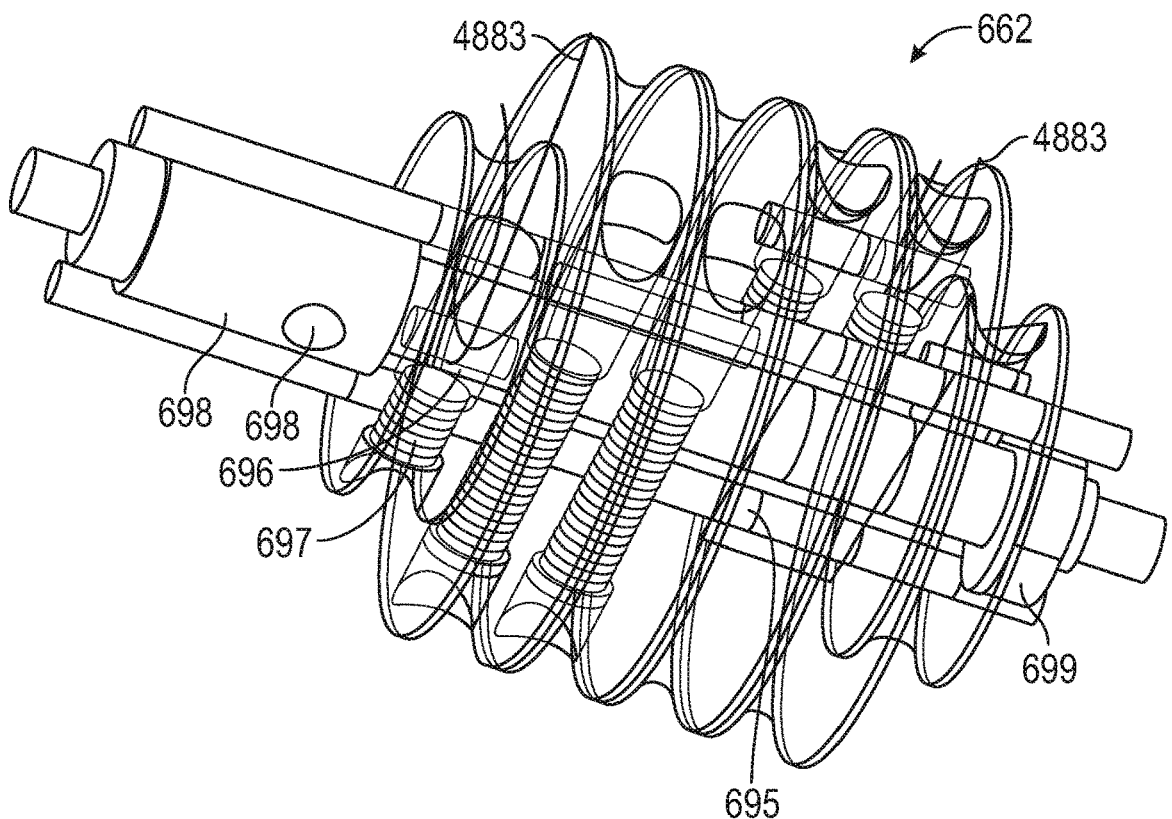

A close-up of the spool stack 662 of the steering catheter handle 600 is shown in FIGS. 6B and 6C. The spool stack 662 includes a plurality of pins 695 that holds the spools aligned to rotate together. The pins 695 can hit travel stops 696 to prevent over-rotation that might damage the pullwires and/or catheter during use. The proximal ends of the pullwires 4883 are wrapped around the pins 695 and pulled to tension. A plurality of set screws 697 tighten down to sandwich the caps 696 against the pins 695, thereby locking the pullwire tension. The caps 696 are contoured pieces that abut the pins 695 without rotating and/or rubbing against them. The spool stack 662 further includes a shaft 698 over which the worm gear 661 is attached. A nut 699 locks down the stack of spools against one another.

Referring to FIGS. 7A-7F, the introducer handle 700 (of system 400) can be configured to attach to the introducer 333. The introducer handle 700 can include a pullwire 775 (see FIG. 7B) to activate bending of the introducer 333. Further, the introducer handle 700 can include a lock knob 771 for rotationally locking and unlocking the handle 700 and introducer 333 relative to the inner steering catheter 4816. An activation knob 772 with teeth can be used to lock the angle of the bend of the introducer 333. The steering catheter 4816 can run through the middle of the handle 700. The activation knob 772 can have a proximal position that allows free spinning (and movement of the pullwire 775) in either direction. The activation knob 772 can also have a distal position that locks against the teeth 773 to prevent rotation, locking the bend of the introducer 333 in place. When locked, ratcheting motion is prevented, as the teeth 773 can have vertical edges to prevent rotation in either direction A ball plunger 774 and a keyed sleeve can set the proximal/distal position of the knob 772. The handle 700 can further include a lead screw 777, which can be rotated when turning the knob 772. The pullwire 775 can be clamped against the leadscrew 777 by set screw clamps 776. Turning the knob 772 therefore rotates the lead screw, which releases or tightens the pullwire 775. Seals 778 (e.g., o-rings) can be used to maintain hemostasis.

Figure 7A:
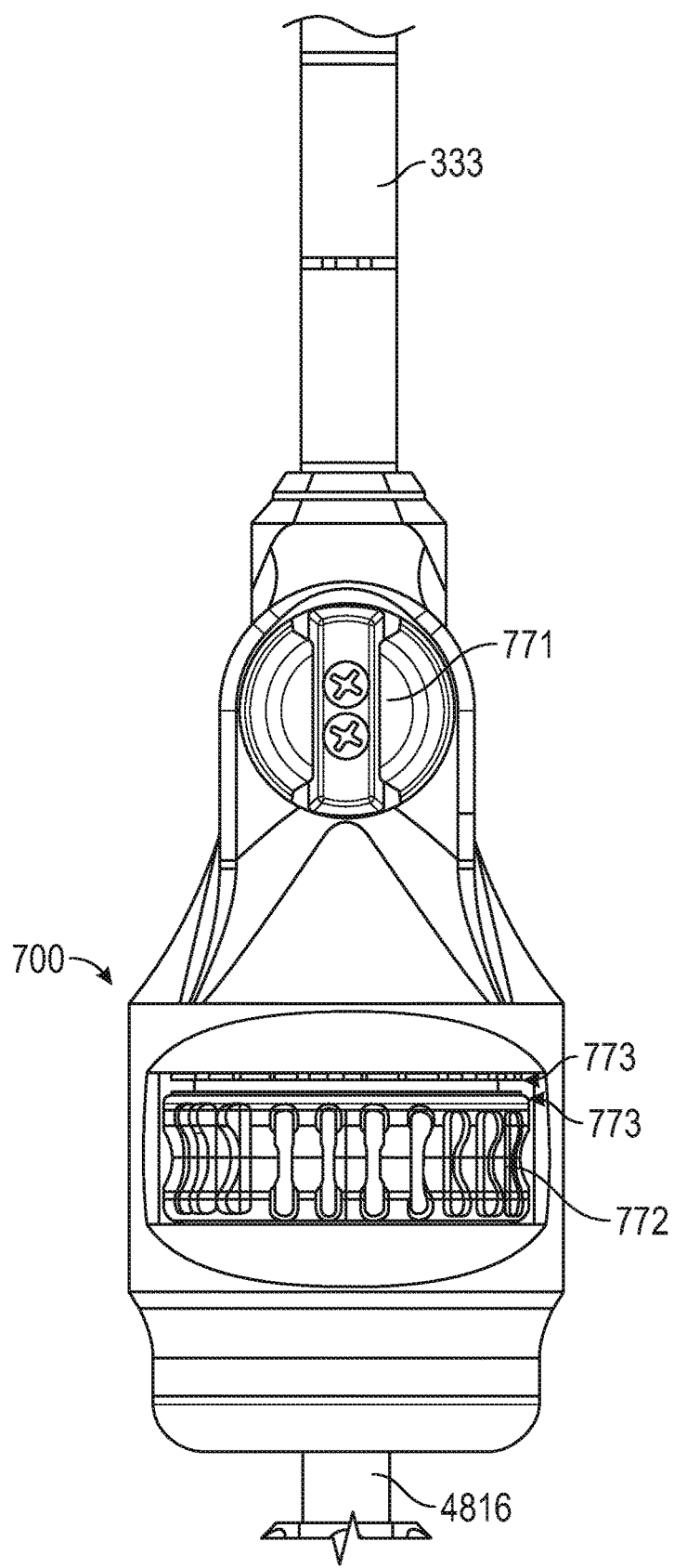
FIGS. 7A-7G show the introducer handle of the system of FIG. 4.
Figure 7B:
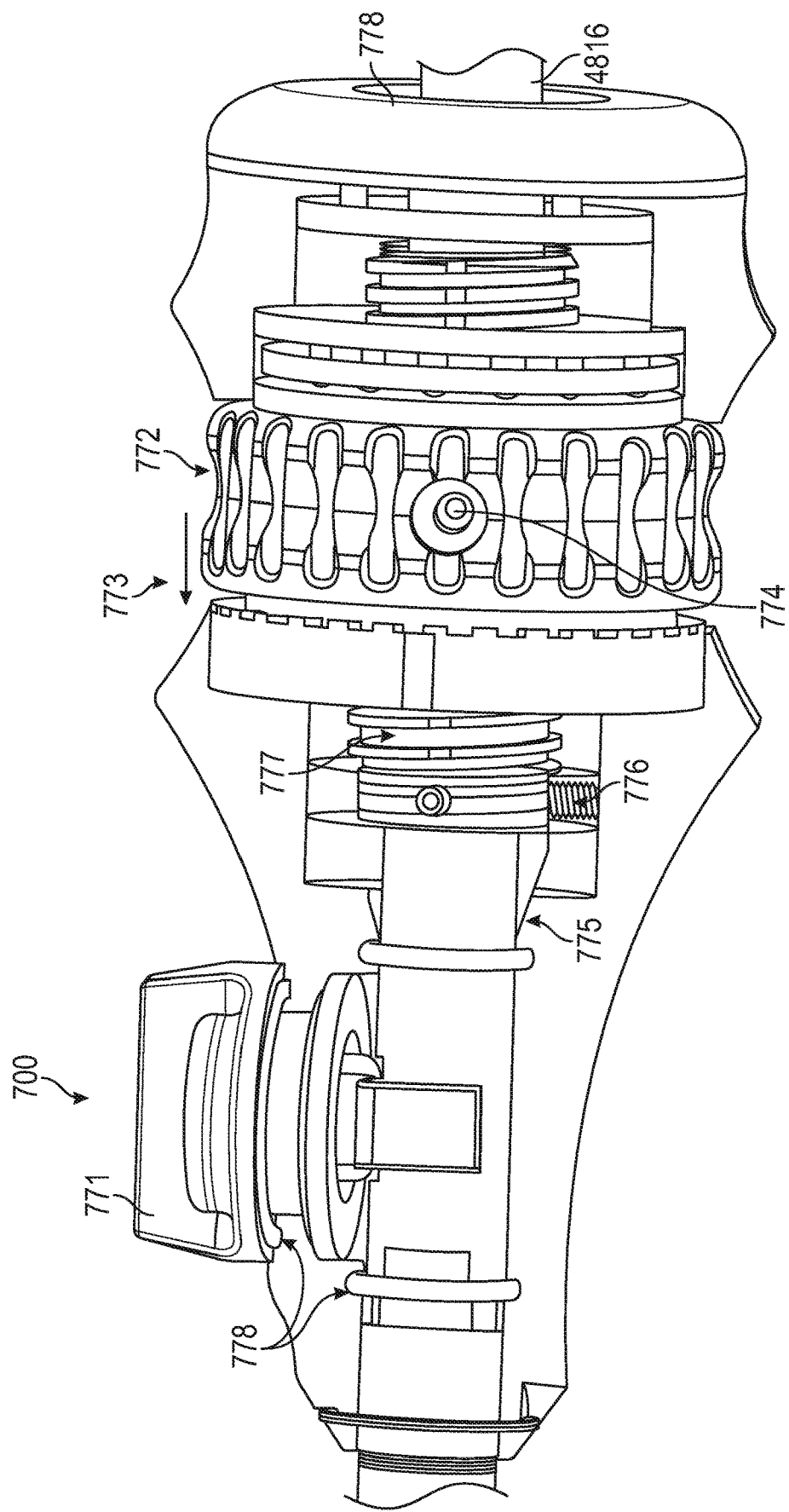
Figure 7C:
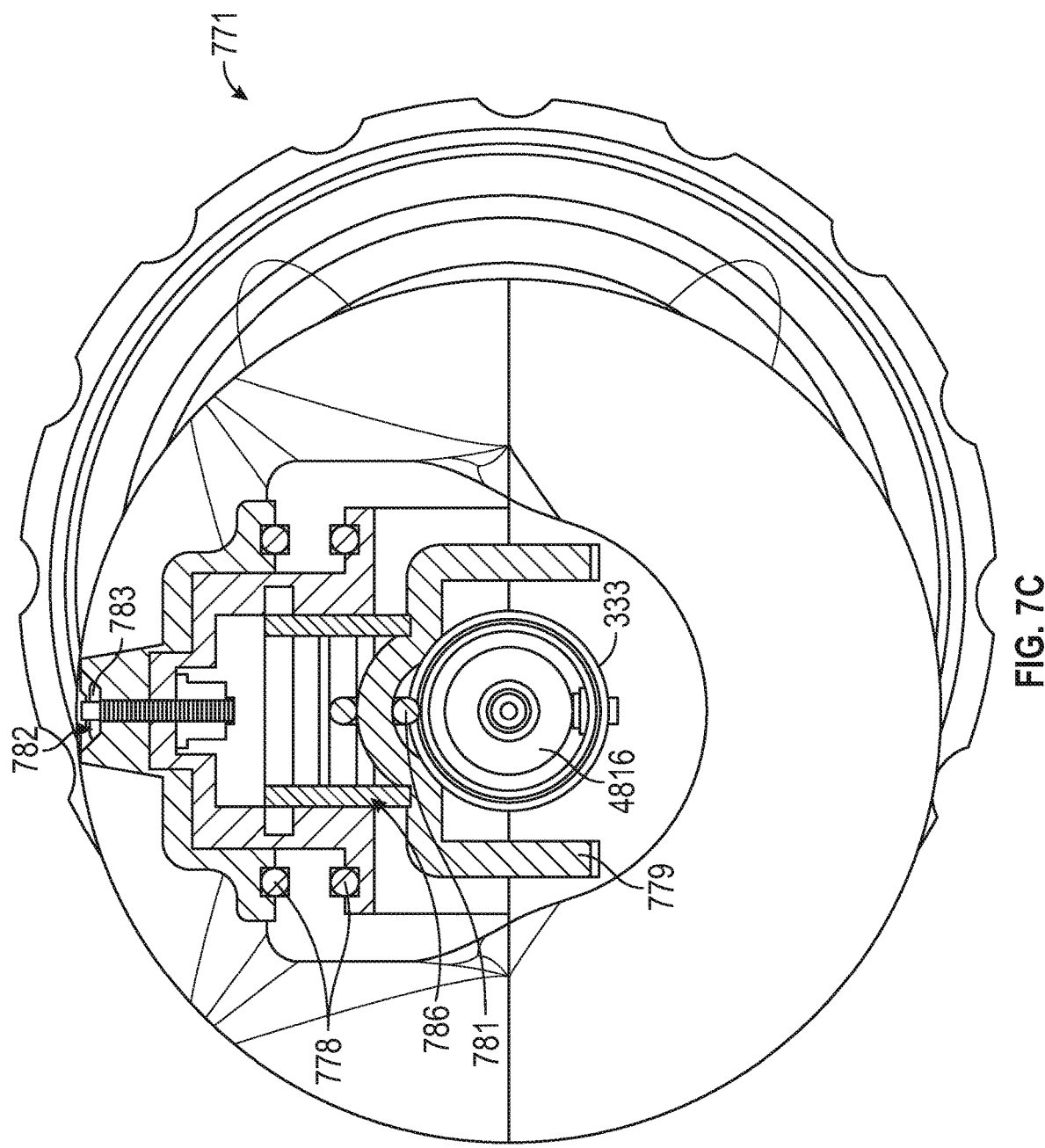
Figure 7D:
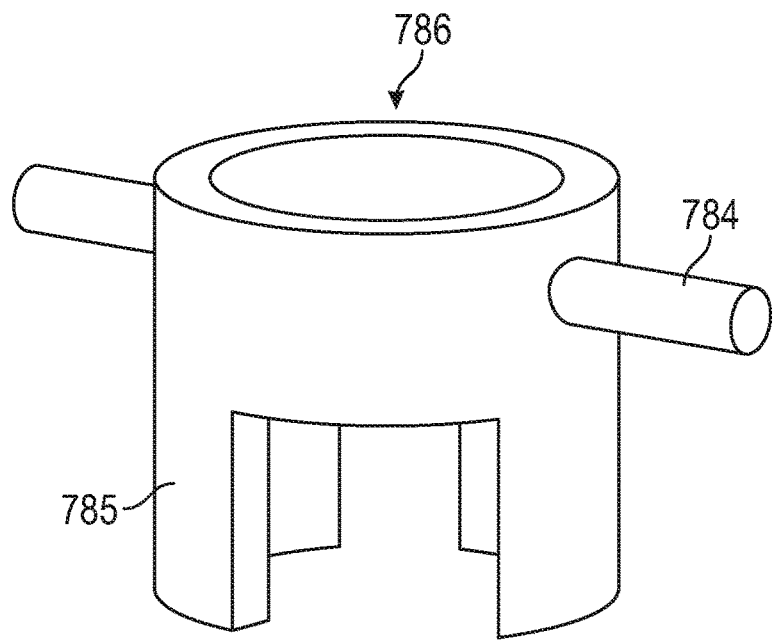
Figure 7E:
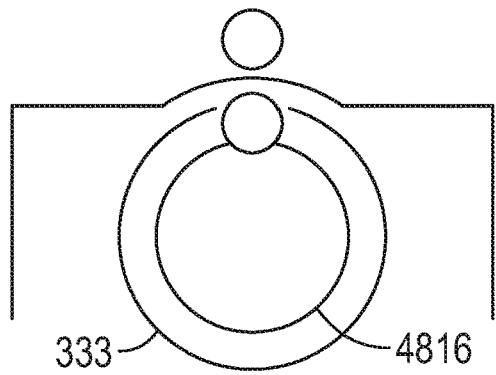
Figure 7F:
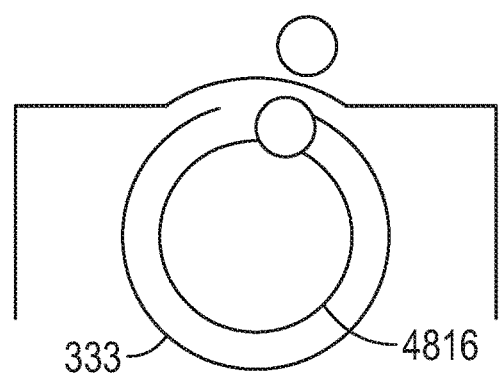
Figure 7G:
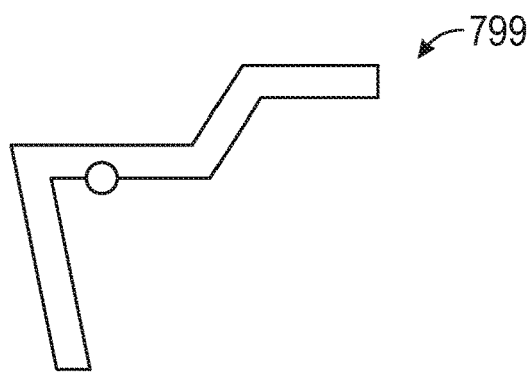

The lock knob 771 of the introducer handle 700 is best shown in FIGS. 7C-7G. The knob 771 can include an o-ring 781 that is raised and lowered to release or grasp the steering catheter 4816. When grasped against the steering catheter 4816 (as shown in FIGS. 7E and 7F), rotation of the steering catheter 4816 relative to the handle 700 will be prevented, but linear insertion/retraction can still occur. A guide piece 779 can align with slots across the handle 700, thereby keeping the guide piece 779 and o-ring from spinning with the knob 771. As shown in FIGS. 7C-7F, a lock tube 786 can be attached to the guide piece 779 and have a pin 784 extending therethrough. A screw and nut 782 can sandwich the inner and outer lock knob pieces together, compressing the o-ring 781 and hemostasis sealing rings 778. Further, the o-ring 781 can be affixed to the guide piece 779, and the guide piece 779 can be attached to tube 786, preventing it from rotating. The pin 784 through tube 786 can sit in two slots in the inner portion of knob 771. The path 799 of these slots is illustrated in 7G. The vertical portion of the path 799 can be used for assembly. In use of the lock knob 771, the ends of the pin 784 sit in the lowered o-ring 781 or raised o-ring 781 portions of the opposing slot patterns. The pin 784 is held in one orientation because the lock tube 786 and the guide piece 779 are joined. Therefore, as the lock knob 771 rotates, this path 799 moves relative to the pin 784. The pin 784 is guided up or down the ramp between the two horizontal regions of the slotted path 799, transitioning from raised and lowered positions. When the o-ring 781 is lowered, rotating the steering catheter is made difficult or impossible as the o-ring 781 provides friction and mechanical interference, wedging against the catheter.

Figure 8:
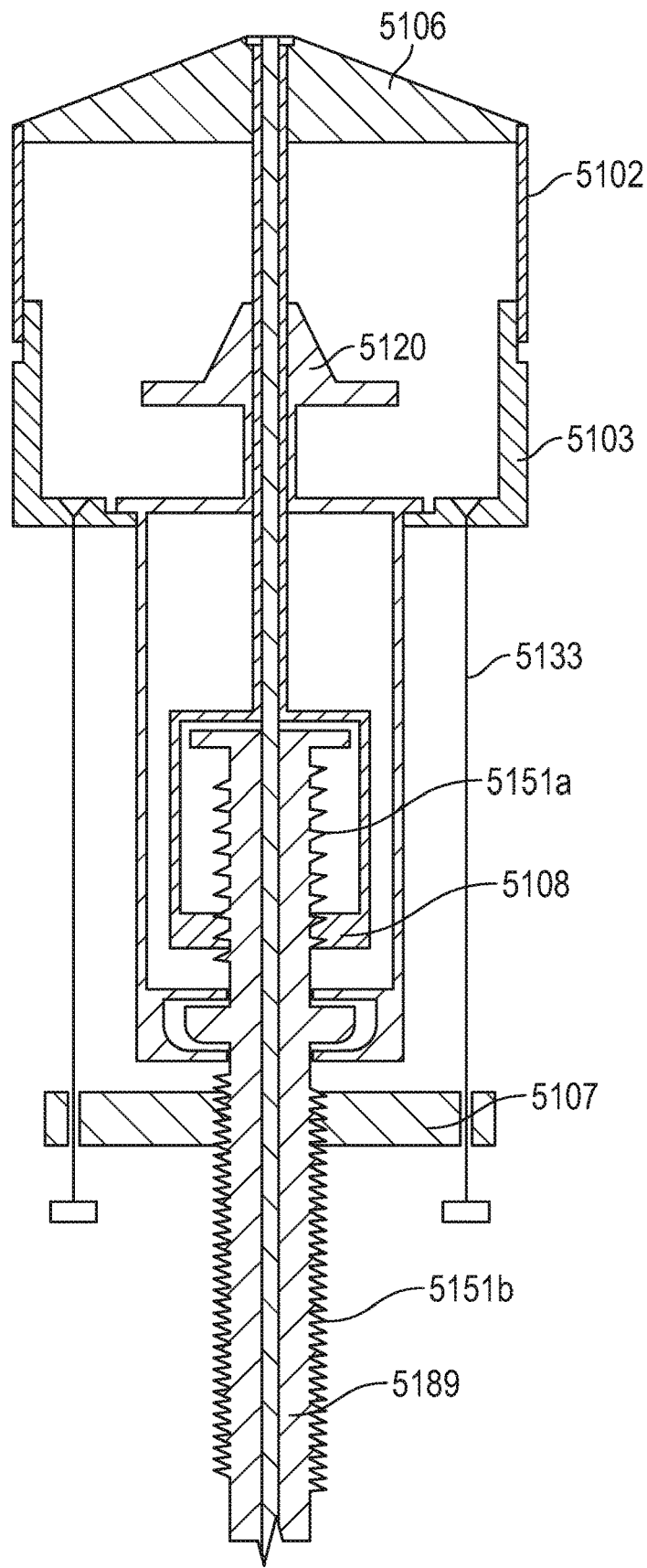
FIG. 8 shows the distal portion of another embodiment of an exemplary transseptal delivery system.

The distal portion of another embodiment of an exemplary transseptal delivery system is shown in FIG. 8. In this embodiment, a compression coil is not used inside of the helical strand 5189. Instead, the helical strand 5189 includes two different sets of threads. The distal thread 5151a extends in one direction (i.e., clockwise or counterclockwise) while the proximal thread 5151b extends in the opposite direction. The proximal and distal threads 5151a,b can be positioned such that rotation of the helical strand 5189 first causes engagement of the distal thread 5151a with a distal nut 5108 that is attached to the nosecone 5106 and distal sheath 5102, causing the nosecone 5016 and distal sheath 5012 to move distally. After a set amount of rotation of the helical strand 5189, the proximal thread 5151b can then engage with the proximal nut 5107 (connected to proximal sheath 5103, for example, via pullwires 5133), thereby causing the proximal sheath 5103 to move proximally. In some embodiments, the pitch of the threads 5151a,b can be different from one another to allow for deployment of the proximal and distal sheaths 5103, 5102 at different speeds. A free spinning florette tether retainer 5120 can be used to hold the loops of the proximal anchor of the valve in place.

Figure 9:
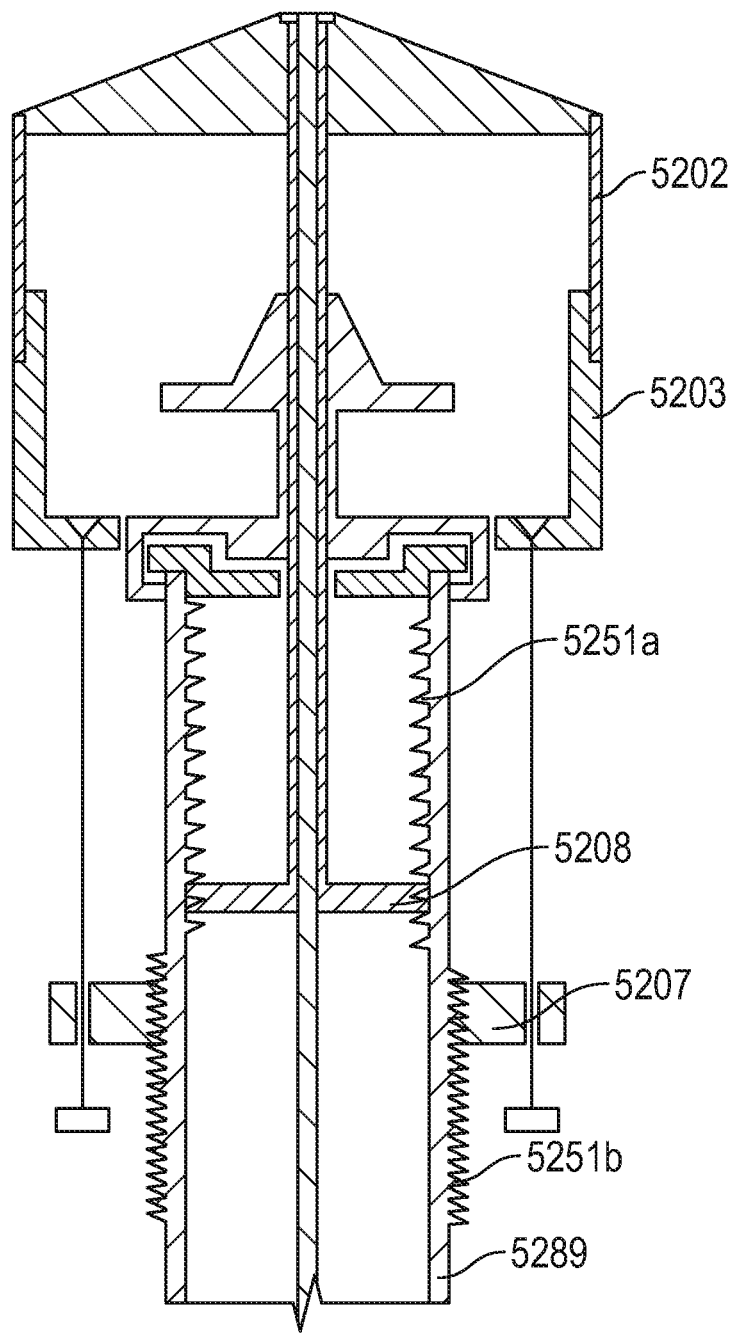
FIG. 9 shows the distal portion of another embodiment of an exemplary transseptal delivery system.

The distal portion of another embodiment of an exemplary transseptal delivery system is shown in FIG. 9. This embodiment is similar to that of FIG. 8 except that the distal threads 5251a are on the internal surface of the helical strand 5289. Similarly, the distal nut 5208 is positioned inside of the helical strand 5289. As in the embodiment of FIG. 8, rotation of the helical strand 5189 will cause the distal threads 5251a to first engage with the distal nut 5208 to extend the distal sheath 5202 distally and then cause the proximal threads 5251b to engage with the proximal nut 5207 to pull the proximal sheath 5203 proximally.

In some embodiments, an additional introducer can be used to help introduce the transseptal delivery systems into the body. For example, referring to FIGS. 10A-C, an introducer 5757 can include a handle 5771 attached to an elongate member 5772. The elongate member 5772 can have a rigid proximal portion 5773 and a flexible distal portion 5774. The flexible portion 5774 can include threads on the exterior thereof to allow the introducer 5757 to screw into place. Further, the pitch on the threads can decrease from the distal end to the proximal end to gently pinch the tissue therebetween (i.e., the progressive pitch decrease can help with progressively catching tissue therebetween). In some embodiments, an annular stopper 5776 can extend around the rigid proximal portion 5773.

Figure 10B:
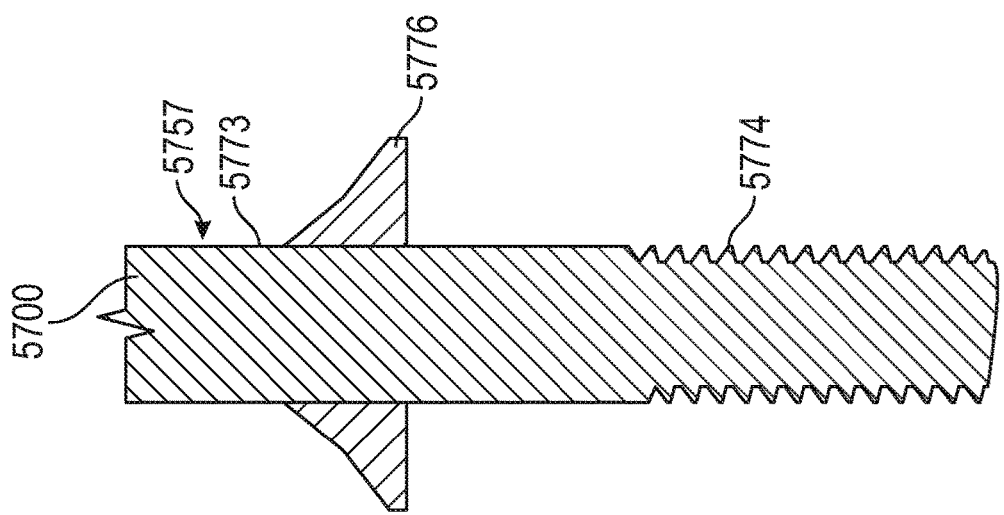
FIGS. 10A-10C show another exemplary introducer.
Figure 10A:
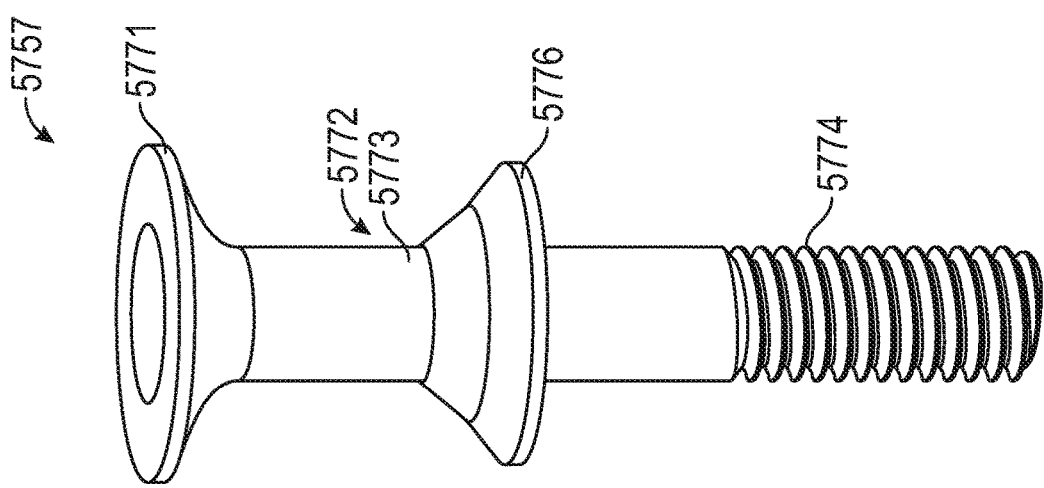
Figure 10C:
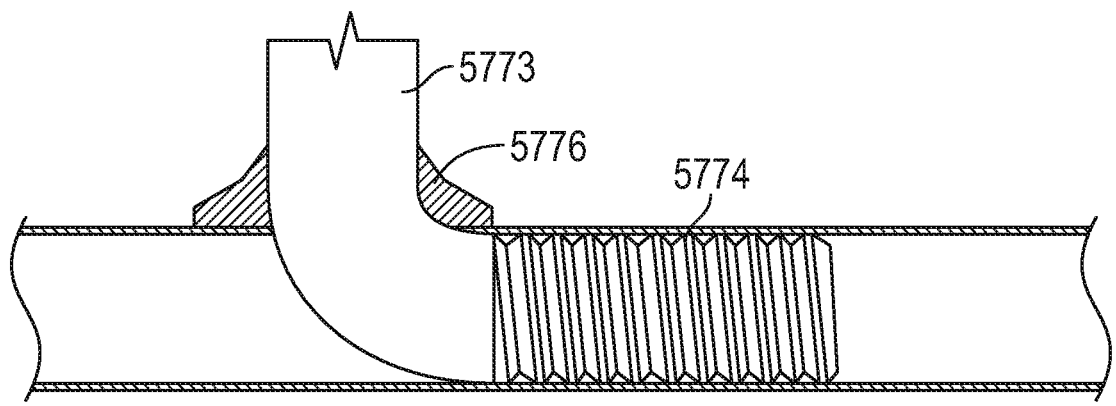

Referring to FIG. 10B, in use, the introducer 5757 can be inserted into the body until the stopper 5776 hits the anatomy at the access site. A transseptal delivery device 5700 can then be passed therethrough. As shown in FIG. 10C, the flexible distal portion 5774 can advantageously flex with the bends of the delivery device 5700 as it is inserted therethrough. The introducer 5757 can be used in place of the steerable catheter 4816 and introducer sheath 333 described herein or can be added to the proximal region of the steerable catheter 4816.

Although described as being used for the transseptal delivery method, the delivery devices described herein can also be used for a trans atrial or surgical delivery methods.

Aspects of the delivery devices and methods may be combined with aspects of the delivery devices and methods described in U.S. patent application Ser. No. 14/677,320, U.S. Pat. No. 8,870,948, or International Patent Application filed May 13, 2016 and titled "REPLACEMENT MITRAL VALVES," the entirety of which is incorporated by reference herein.

Although described herein for use with a mitral valve prosthetic, the delivery systems described herein can be used with a variety of different implantable devices, including stents or other valve prosthetics.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A prosthetic valve delivery system, comprising:
   a handle; and
   a delivery catheter comprising:
      a central elongate member extending from the handle; and
      a split sheath configured to slide over and relative to the central elongate member, the split sheath and the central elongate member together defining a compartment for holding a prosthetic valve in a collapsed condition, the split sheath having a proximal sheath portion and a distal sheath portion;
      a threaded nut connected to the proximal sheath portion;
      a hollow helical strand engageable with the threaded nut such that rotation of the hollow helical strand in a first direction causes retraction of the proximal sheath portion to expose at least a portion of the prosthetic valve; and
      a control knob in the handle and connected to the hollow helical strand such that rotation of the control knob rotates the hollow helical strand in the first direction to retract the proximal sheath portion.

2. The delivery system of claim 1, further comprising a valve retainer at a distal end of the central elongate member.

3. The delivery system of claim 2, wherein the valve retainer is a florette.

4. The delivery system of claim 1, wherein the distal sheath is connected to a compression coil configured to be pushed distally to move the distal sheath distally.

5. The delivery system of claim 1, further comprising a steering catheter configured to be positioned radially over the delivery catheter, the steering catheter comprising a steerable distal end.

6. The delivery system of claim 5, wherein the steerable distal end comprises a plurality of articulating segments.

7. The delivery system of claim 6, further comprising a plurality of pullwires, each pullwire being connected to a different articulating segment to control articulation of the distal end.

8. The delivery system of claim 5, further comprising an introducer configured to be positioned radially over the steering catheter, the introducer comprising a bent or bendable distal section.

9. The delivery system of claim 8, wherein the introducer is configured to be axially and rotationally movable relative to the steering catheter.

10. The delivery system of claim 8, further comprising a sealing valve between the steering catheter and the introducer.

11. The delivery system of claim 8, wherein the handle comprises a delivery catheter portion, a steering catheter portion, and an introducer portion.

12. The delivery system of claim 11, wherein the delivery catheter portion and the steering catheter portion are connected together with a telescoping tube such that the delivery catheter portion is axially movable relative to the steering catheter portion.

13. The delivery system of claim 11, wherein the steering catheter portion and the introducer portion are connected together with a telescoping tube such that the introducer portion is axially and rotationally movable relative to the steering catheter portion.

14. A prosthetic valve delivery system, comprising:
   a handle;
   a delivery catheter comprising:
      a central elongate member extending from the handle;
      a split sheath configured to slide over and relative to the central elongate member the split sheath and the central elongate member together defining a compartment for holding a prosthetic valve in a collapsed condition, the split sheath having a proximal sheath portion and a distal sheath portion;
      a threaded nut connected to the proximal sheath portion;
      a hollow helical strand engageable with the threaded nut such that rotation of the hollow helical strand in a first direction causes retraction of the proximal sheath portion to expose at least a portion of the prosthetic valve; and
      a control knob in the handle and connected to the hollow helical strand such that rotation of the control knob rotates the hollow helical strand in the first direction to retract the proximal sheath portion; and
   a steering catheter configured to be positioned radially over the delivery catheter, the steering catheter comprising a steerable distal end.

15. The delivery system of claim 14, further comprising a valve retainer at a distal end of the central elongate member.

16. The delivery system of claim 15, wherein the valve retainer is a florette.

17. The delivery system of claim 14, wherein the distal sheath is connected to a compression coil configured to be pushed distally to move the distal sheath distally.

18. The delivery system of claim 14, wherein the steerable distal end comprises a plurality of articulating segments.

19. The delivery system of claim 18, further comprising a plurality of pullwires, each pullwire being connected to a different articulating segment to control articulation of the distal end.

20. The delivery system of claim 14, further comprising an introducer configured to be positioned radially over the steering catheter, the introducer comprising a bent or bendable distal section.

21. The delivery system of claim 20, wherein the introducer is configured to be axially and rotationally movable relative to the steering catheter.

22. The delivery system of claim 20, further comprising a sealing valve between the steering catheter and the introducer.

23. The delivery system of claim 20, wherein the handle comprises a delivery catheter portion, a steering catheter portion, and an introducer portion.

24. The delivery system of claim 23, wherein the delivery catheter portion and the steering catheter portion are connected together with a telescoping tube such that the delivery catheter portion is axially movable relative to the steering catheter portion.

25. The delivery system of claim 23, wherein the steering catheter portion and the introducer portion are connected together with a telescoping tube such that the introducer portion is axially and rotationally movable relative to the steering catheter portion.

* * * * *